United States Patent
Ishii et al.

(10) Patent No.: US 10,179,763 B2
(45) Date of Patent: Jan. 15, 2019

(54) OXIDE CATALYST AND METHOD FOR PRODUCING SAME, AND METHOD FOR PRODUCING UNSATURATED NITRILE

(71) Applicant: ASAHI KASEI KABUSHIKI KAISHA, Tokyo (JP)

(72) Inventors: Yusuke Ishii, Tokyo (JP); Kazushi Okada, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/102,950

(22) PCT Filed: Mar. 4, 2015

(86) PCT No.: PCT/JP2015/056317
§ 371 (c)(1),
(2) Date: Jun. 9, 2016

(87) PCT Pub. No.: WO2015/133510
PCT Pub. Date: Sep. 11, 2015

(65) Prior Publication Data
US 2016/0297753 A1    Oct. 13, 2016

(30) Foreign Application Priority Data
Mar. 6, 2014  (JP) ................. 2014-044235

(51) Int. Cl.
| C07C 253/24 | (2006.01) |
| B01J 37/04 | (2006.01) |
| B01J 23/30 | (2006.01) |
| B01J 37/02 | (2006.01) |
| B01J 23/00 | (2006.01) |
| B01J 21/08 | (2006.01) |
| B01J 35/00 | (2006.01) |
| B01J 37/08 | (2006.01) |
| B01J 37/00 | (2006.01) |

(52) U.S. Cl.
CPC ............. *C07C 253/24* (2013.01); *B01J 21/08* (2013.01); *B01J 23/002* (2013.01); *B01J 23/30* (2013.01); *B01J 35/0006* (2013.01); *B01J 37/0215* (2013.01); *B01J 37/0236* (2013.01); *B01J 37/04* (2013.01); *B01J 37/088* (2013.01); *B01J 37/009* (2013.01); *B01J 37/0045* (2013.01); *B01J 2523/00* (2013.01); *Y02P 20/52* (2015.11)

(58) Field of Classification Search
CPC .................................................... C07C 253/24
See application file for complete search history.

(56) References Cited

U.S. PATENT DOCUMENTS

| 6,037,304 | A | 3/2000 | Abdulwahed et al. |
| 8,105,971 | B2 * | 1/2012 | Gaffney ............... B01J 23/002 |
| | | | 502/178 |
| 2002/0115879 | A1 | 8/2002 | Hinago et al. |
| 2008/0108843 | A1 | 5/2008 | Kato et al. |
| 2009/0198081 | A1 | 8/2009 | Paparizos et al. |
| 2011/0218352 | A1 | 9/2011 | Besecker et al. |
| 2013/0053596 | A1 | 2/2013 | Kato et al. |
| 2013/0253217 | A1 | 9/2013 | Ishii et al. |

FOREIGN PATENT DOCUMENTS

| JP | 2002-239382 A | 8/2002 |
| JP | 2006-55681 A | 3/2006 |
| JP | 2011-529777 A | 12/2011 |
| JP | 2013-169482 A | 9/2013 |
| JP | 2013-198902 A | 10/2013 |
| KR | 10-2012-0123554 A | 11/2012 |
| WO | WO 2012/090979 A1 | 7/2012 |

OTHER PUBLICATIONS

No new references.*
Supplementary European Search Report, dated Feb. 23, 2017, for European Application No. 15759280.9.
International Preliminary Report on Patentability and an English translation of the Written Opinion of the International Searching Authority issued in the corresponding International Application No. PCT/JP2015/056317 dated Sep. 15, 2016.
International Search Report, issued in PCT/JP2015/056317, PCT/ISA/210, dated May 19, 2015.
Written Opinion of the International Searching Authority, issued in PCT/JP2015/056317, PCT/ISA/237, dated May 19, 2015.

* cited by examiner

*Primary Examiner* — Shawquia Jackson
(74) *Attorney, Agent, or Firm* — Birch, Stewart, Kolasch & Birch, LLP

(57) ABSTRACT

There is provided a method for producing an oxide catalyst, the method including a step (a) of obtaining an aqueous mixed liquid A containing Mo, V and Sb, a step (b) of mixing a Nb raw material, water and an organic acid to obtain a Nb aqueous solution, a step (c) of mixing the Nb aqueous solution and a silica raw material to obtain an aqueous mixed liquid B, a step (d) of mixing the aqueous mixed liquid A and the aqueous mixed liquid B to obtain an aqueous mixed liquid (C), a step (e) of drying the aqueous mixed liquid C to obtain a dried powder D, and a step (f) of calcining the dried powder D to obtain the oxide catalyst.

5 Claims, No Drawings

OXIDE CATALYST AND METHOD FOR PRODUCING SAME, AND METHOD FOR PRODUCING UNSATURATED NITRILE

TECHNICAL FIELD

The present invention relates to an oxide catalyst and a method for producing the oxide catalyst, and a method for producing an unsaturated nitrile.

BACKGROUND ART

At the present day, an unsaturated nitrile which is generally available commercially is mainly produced industrially by the vapor-phase catalytic ammoxidation reaction of olefin, ammonia, and oxygen. On the other hand, in recent years, a method for subjecting an alkane such as propane or isobutane as a feedstock in place of the olefin to a vapor-phase catalytic ammoxidation reaction to produce a corresponding unsaturated nitrile has attracted much attention. Various catalysts used in the case have also been proposed.

Patent Literature 1 describes a method for producing a catalyst to be used for the vapor-phase catalytic oxidation or vapor-phase catalytic ammoxidation of propane or isobutane. The method for producing a catalyst described in Patent Literature 1 comprises a step of drying and calcining a raw material blending liquid obtained by the following steps (1) to (4):

a step (1) of preparing an aqueous mixed liquid comprising Mo, V and Sb;

a step (2) of adding silica sol and hydrogen peroxide water to the aqueous mixed liquid obtained in the above step (1);

a step (3) of mixing the solution obtained in the above step (2) with an aqueous solution comprising Nb, dicarboxylic acid and hydrogen peroxide water, and a W-containing compound; and a step (4) of adding a powder silica-containing suspension liquid to the solution obtained in the above step (3).

CITATION LIST

Patent Literature

Patent Literature 1: International Publication No. WO2012/090979

SUMMARY OF INVENTION

Technical Problem

Although catalysts used for the vapor-phase catalytic ammoxidation reaction or the like of propane are improved in their performance due to improvements thereof, catalysts exhibiting a much higher yield are industrially demanded. On the other hand, accompanying the improvement in the catalyst performance, catalyst production step are complicated and the industrial catalyst production is made difficult.

The present invention has been accomplished in view of the above-mentioned problems, and has an object to provide an oxide catalyst exhibiting a higher performance than conventional ones, without needing the introduction of complicated steps and the variations of facilities, and a method for producing the oxide catalyst, and a method for producing an unsaturated nitrile using the oxide catalyst.

Solution to Problem

The present inventors have paid attention to the relationship between a carrier and metal components, and studied a method for simply controlling the distribution of the metal components in an oxide catalyst. As a result, it has been found that when a Nb species is firstly dispersed on the carrier, the above-mentioned problem can be solved, and this finding has led to the completion of the present invention.

As a result of exhaustive studies on a method for producing a silica-supported catalyst containing, for example, molybdenum, vanadium, antimony and niobium, it has been found that after an aqueous mixed liquid A containing molybdenum, vanadium and antimony is prepared and a mixed liquid (B) of a niobium raw material and a silica raw material is separately prepared, the above liquids (A) and (B) are mixed to be thereby able to produce the silica-supported catalyst in which metal components as catalytically active species are uniformly dispersed, and this finding has led to the present invention.

That is, the present invention is as follows.

[1]
A method for producing an oxide catalyst, the method comprising:

a step (a) of obtaining an aqueous mixed liquid A comprising Mo, V and Sb;

a step (b) of mixing a Nb raw material, water and an organic acid to obtain a Nb aqueous solution;

a step (c) of mixing the Nb aqueous solution and a silica raw material to obtain an aqueous mixed liquid B;

a step (d) of mixing the aqueous mixed liquid A and the aqueous mixed liquid B to obtain an aqueous mixed liquid C;

a step (e) of drying the aqueous mixed liquid C to obtain a dried powder D; and a step (f) of calcining the dried powder D to obtain the oxide catalyst.

[2]
The method for producing the oxide catalyst according to [1], wherein a molar ratio (Nb/Si) of Nb to 1 mol of Si in the aqueous mixed liquid B is 0.02 to 0.7.

[3]
The method for producing the oxide catalyst according to [1] or [2], wherein in the step (c), a mixing time of the Nb aqueous solution and the silica raw material is 1 minute to 6 hours.

[4]
The method for producing the oxide catalyst according to any one of [1] to [3], comprising, after the step (d) and before the step (e), a step (d') of mixing the aqueous mixed liquid C and powder silica and/or silica sol.

[5]
The method for producing the oxide catalyst according to any one of [1] to [4], wherein a content of silica in the oxide catalyst is 20 to 70% by mass in terms of $SiO_2$.

[6]
The method for producing the oxide catalyst according to any one of [1] to [5], wherein the oxide catalyst contains a metal component represented by the following formula (1):

$$Mo_1V_aSb_bNb_cW_dZ_eO_n \qquad (1),$$

wherein Z is at least one element selected from the group consisting of La, Ce, Pr, Yb, Y, Sc, Sr, and Ba; a, b, c, d, e, and n represent atomic ratios of each element and satisfy $0.1 \leq a \leq 0.3$, $0.15 \leq b \leq 0.5$, $0.01 \leq c \leq 0.5$, $0 \leq d \leq 0.4$, and $0.5 \leq e \leq 0.2$, and n is a number determined by a, b, c, d and e.

[7]
A method for producing an unsaturated nitrile, comprising a step of subjecting propane or isobutane to a vapor-phase catalytic oxidation reaction or a vapor-phase catalytic ammoxidation reaction with an oxide catalyst obtained by the method for producing the oxide catalyst according to any one of [1] to [6], to produce a corresponding unsaturated nitrile.

[8]

An oxide catalyst, being produced by the method for producing the oxide catalyst according to any one of [1] to [6].

Advantageous Effects of Invention

The present invention can provide an oxide catalyst exhibiting a higher performance and a method for producing the oxide catalyst, without needing the introduction of complicated steps and the variations of facilities, and a method for producing the unsaturated nitrile using the oxide catalyst.

DESCRIPTION OF EMBODIMENTS

Hereinafter, a mode for carrying out the present invention (hereinafter, merely referred to as "present embodiment") will be described in detail. The following present embodiment is given in order to illustrate the present invention. The present invention should not be construed to be limited to the following contents. The present invention may be carried out while making appropriate modification within the scope of the invention.

[Oxide Catalyst]

A method for producing an oxide catalyst according to the present embodiment comprises:

a step (a) of obtaining an aqueous mixed liquid A comprising molybdenum (Mo), vanadium (V) and antimony (Sb);

a step (b) of mixing a niobium (Nb) raw material, water and an organic acid to obtain a Nb aqueous solution;

a step (c) of mixing the Nb aqueous solution and a silica raw material to obtain an aqueous mixed liquid B;

a step (d) of mixing the aqueous mixed liquid A and the aqueous mixed liquid B to obtain an aqueous mixed liquid C;

a step (e) of drying the aqueous mixed liquid C to obtain a dried powder D; and a step (f) of calcining the dried powder D to obtain the oxide catalyst.

[Step (a)]

In the step (a), an aqueous mixed liquid A comprising Mo, V and Sb is obtained. More specifically, a raw material comprising Mo, a raw material comprising V, and a raw material comprising Sb are mixed to obtain the aqueous mixed liquid A.

The raw material comprising Mo (hereinafter, also referred to as "Mo raw material") is not particularly limited, but examples thereof include ammonium heptamolybdate [$(NH_4)_6Mo_7O_{24} \cdot 4H_2O$], molybdenum trioxide [$MoO_3$], phosphomolybdic acid [$H_3PMo_{12}O_{40}$], silicomolybdic acid [$H_4SiMo_{12}O_{40}$], and molybdenum pentachloride [$MoC_{15}$] or the like. Among them, ammonium heptamolybdate is preferable.

The raw material comprising V (hereinafter, also referred to as "V raw material") is not particularly limited, but examples thereof include ammonium metavanadate [$NH_4VO_3$], vanadium pentoxide [$V_2O_5$], and vanadium chloride [$VCl_4$, $VCl_3$] or the like. Among them, ammonium metavanadate is preferable.

The raw material comprising Sb (hereinafter, also referred to as "Sb raw material") is not particularly limited, but examples of thereof include antimony oxide [$Sb_2O_3$, $Sb_2O_5$], antimonious acid [$HSbO_2$], antimonic acid [$HSbO_3$], ammonium antimonate [$(NH4)SbO_3$], antimony chloride [$Sb_2Cl_3$], and an organic acid salt such as a tartrate of antimony, and metal antimony or the like. Among them, diantimony trioxide is preferable.

The aqueous mixed liquid A may further contain tungsten (W). More specifically, the aqueous mixed liquid A may be mixed further with a raw material comprising W. A raw material comprising W (hereinafter, also referred to as "W raw material") is not particularly limited, but examples of thereof include a tungsten salt such as an ammonium salt, a nitrate, a carboxylate, ammonium carboxylate, a peroxocarboxylate, ammonium peroxocarboxylate, a halogenated ammonium salt, a halide, acetylacetonate, an alcoxide, a triphenyl compound, a polyoxometalate, ammonium polyoxometalate; tungsten trioxide, tungsten dioxide, tungstic acid, an ammonium metatungstate, ammonium paratungstate, tungstosilicic acid, silicotungstomolybdic acid, and tungstosilicic acid or the like. Among them, the ammonium metatungstate is preferable. It is preferable that the W raw material is previously mixed in water and is used as an aqueous solution.

The aqueous mixed liquid A may further contain one or more elements (hereinafter, referred to as "Z") selected from the group consisting of La, Ce, Pr, Yb, Y, Sc, Sr and Ba. More specifically, the aqueous mixed liquid A may further be mixed with a raw material comprising Z (hereinafter, also referred to as "Z raw material"). The raw material comprising Z is not particularly limited, but examples of thereof include a compound comprising Z, or Z solubilized by an appropriate reagent. The compound comprising Z is not particularly limited, but examples of thereof include an ammonium salt, a nitrate, a carboxylate, an ammonium carboxylate, a peroxocarboxylate, an ammonium peroxocarboxylate, a halogenated ammonium salt, a halide, acetylacetonate, or an alkoxide of Z. Among them, an aqueous raw material such as a nitrate or a carboxylate is preferable.

In the step (a), the dissolution procedure, the mixing procedure or the dispersion procedure of the Mo raw material, the V raw material and the Sb raw material, and as added if needed, the W raw material and the Z raw material are not particularly limited. Each raw material may be dissolved, mixed or dispersed in the same aqueous medium. Alternatively, the raw materials may be individually dissolved, mixed or dispersed in aqueous media, and then, the aqueous media may be mixed. Heating and/or stirring may be performed if needed.

One example of the step (a) will be described in detail. The Mo raw material, the V raw material, and the Sb raw material are mixed with water, and heated to prepare an aqueous mixed liquid A. At this time, a Z raw material may be added. A heating temperature and a heating time when the aqueous mixed liquid A is prepared are preferably adjusted such that the each raw material can be sufficiently dissolved. The heating temperature is preferably 70° C. to 100° C.; and the heating time is preferably 30 minutes to 5 hours. At this time, the aqueous mixed liquid A is preferably stirred. At this time, the interior of the vessel may be an air atmosphere, but may be a nitrogen atmosphere from the viewpoint of adjusting the oxidation number of an obtained oxide catalyst. The temperature of the aqueous mixed liquid A is preferably 20° C. or more and 80° C. or less, and more preferably 40° C. or more and 80° C. or less. The temperature of the aqueous mixed liquid A is 20° C. or more, and thereby the deposition of the metal species dissolved in the aqueous mixed liquid A tends to be unlikely to occur.

Further, from the viewpoint of adjusting the oxidation number of the obtained oxide catalyst, an appropriate amount of hydrogen peroxide water is preferably added to the aqueous mixed liquid A if needed. The timing of adding the hydrogen peroxide water is not particularly limited. At this time, from the viewpoint of adjusting the oxidation number of the obtained oxide catalyst to a proper range, the amount of a hydrogen peroxide water to be added to 1 mol of Sb is preferably 0.01 to 5 mol, more preferably 0.5 to 3 mol, and still more preferably 1 to 2.5 mol.

The heating temperature and the heating time after the hydrogen peroxide water is added to the aqueous mixed liquid A are preferably such that a liquid phase oxidation reaction due to the hydrogen peroxide water can sufficiently proceed. The heating temperature is preferably 30° C. to 70° C., and the heating time is preferably 5 minutes to 4 hours. Similarly, the rotation number of stirring during heating can be adjusted to an appropriate rotation number in which the liquid phase oxidation reaction due to the hydrogen peroxide water is likely to proceed. From the viewpoint of causing the liquid phase oxidation reaction due to the hydrogen peroxide water to sufficiently proceed, a stirring state is preferably kept during heating.

[Step (b)]

The step (b) is a step of mixing a Nb raw material (a raw material comprising Nb), water and an organic acid to obtain a Nb aqueous solution. The Nb raw material is not particularly limited, but examples thereof include niobic acid, an inorganic niobate and an organic niobate. Among them, particularly niobic acid is preferable. Niobic acid is represented by $Nb_2O_5.nH_2O$, and is denoted also as niobium hydroxide or a niobium oxide compound. The Nb raw material is preferably used by adding water. At this time, the molar ratio (mol/kg) of Nb to 1 kg of water to be added is, from the viewpoint of stabilizing the Nb compound and the like, preferably 0.1 to 10 mol, more preferably 0.3 to 5 mol, and still more preferably 0.4 to 3 mol.

The organic acid is not particularly limited, but examples thereof include oxalic acid, malonic acid, succinic acid, and glutaric acid. Among them, oxalic acid is preferable. As for the amount of an organic acid to be added, is, to 1 mol of niobium, preferably 1 to 4 mol, more preferably 1.2 to 3.8 mol, and still more preferably 1.5 to 3.5 mol. The amount of an organic acid to be added is 1 mol or more to 1 mol of niobium, and thereby the generation of precipitates originated from niobium tends to be further suppressed. Further the amount of an organic acid to be added is 4 mol or less to 1 mol of niobium, and thereby the oxidation/reduction state of a catalyst is properly held and the catalyst performance tends to be further improved.

A method of mixing a Nb raw material, water and an organic acid is not particularly limited, and these may be mixed in any order. The temperature for the mixing may be any temperature as long as the temperature is a temperature at which a Nb aqueous solution does not freeze or more, and is a temperature at which the Nb aqueous solution does not boil or less. From the viewpoint of the operability and the like, the mixing is preferably performed at room temperature.

A hydrogen peroxide water is preferably added to the Nb aqueous solution. At this time, the amount of a hydrogen peroxide water to be added is, to 1 mol of Nb, preferably 0.5 to 20 mol, more preferably 1 to 10 mol, and still more preferably 1.5 to 5 mol. The amount of a hydrogen peroxide water to be added is in the above range, and thereby a complex with a Nb compound is formed and the Nb compound can be stabilized in a dissolution state, and the oxidation/reduction state of the catalyst-constituting element can properly be adjusted, whereby the catalyst performance of the obtained catalyst tends to be able to be properly adjusted.

[Step (c)]

The step (c) is a step of mixing a Nb aqueous solution and a silica raw material to obtain an aqueous mixed liquid B. Studies by the present inventors have found that in conventional methods for producing the catalyst, if a Nb species and other metal species are mixed in water in the state that the other metal species are present in a higher concentration than the Nb species, the Nb species is not well composited with a silica carrier and uniform dispersion of Nb in the catalyst is difficult. Then as a result of exhaustive studies by paying attention to making a silica raw material and a Nb species to interact each other before the Nb species and the other metal species are mixed, it has been made clear that by introducing a step (c) of previously mixing a Nb species and a silica raw material, the adsorption of the Nb species on a silica carrier is given priority and the uniformity of the metal components can be improved. Further thereby, it has been found that there is more improved the yield of a target product such as an unsaturated nitrile obtained by using an oxide catalyst obtained by the production method according to the present embodiment.

Further the present inventors carried out investigations, and found that the yield of a target such as an unsaturated nitrile is improved when a silica raw material to be used in the step (c) is silica sol. The reason is presumably that a Nb raw material is easily adsorbed to the silica raw material, having many surface silanol groups, and an active species of a catalyst is produced with the Nb raw material as a nucleus and the yield of a target is improved, but is not limited thereto. It is also presumed that if the oxidation/reduction of metal components in an aqueous mixed liquid A is suitably controlled, other metal components are uniformly dispersed on the Nb species on a silica carrier and the selectivity of a target product is improved. From the above-mentioned viewpoint, the silica raw material to be used in the step (c) is preferably silica sol.

Further the aqueous mixed liquid B is preferably added to the aqueous mixed liquid A. Thereby, the nonuniform deposition of the Nb species can be suppressed and the adsorption of the Nb species on a silica carrier can be promoted, whereby the selectivity of an unsaturated nitrile is improved and the yield of the unsaturated nitrile tends to be able to be further improved.

The silica raw material functions as a carrier of the oxide catalyst. The silica raw material is not particularly limited, but for example, a silica sol can be used and powder silica can be used either partially or entirely as the raw material for silica.

The mixing order of a Nb aqueous solution and a silica raw material is not particularly limited. The silica raw material may be added to the Nb aqueous solution, or the Nb aqueous solution may be added to the silica raw material. Among them, from the viewpoint of suppressing deposition of Nb in a Nb aqueous solution, it is more preferable that a silica raw material is added to the Nb aqueous solution. After the addition, the mixture may be left to stand or stirred, and may be subjected to an ultrasonic treatment using a homogenizer or the like. At this time, a part of other metal raw materials may be previously added to a Nb aqueous solution, or a part of the other metal raw materials may be previously added to a silica raw material. The other metal raw materials refer to a Mo raw material, a V raw material, an Sb raw material, a W raw material and a Z raw material. The amount of the other metal raw materials to be added at this time is, with respect to the total amount of the metal raw materials to be finally added, preferably less than 50% by mass, more preferably 0 to 40% by mass, and still more preferably 0 to 30% by mass.

It is preferable as described before that a hydrogen peroxide water is added to a Nb aqueous solution. In the case of adding a hydrogen peroxide water to a Nb aqueous solution, it is preferable that after the hydrogen peroxide water is added to the Nb aqueous solution, the mixture is mixed the a silica raw material.

The temperature at which a silica raw material and a Nb aqueous solution are mixed is preferably 80° C. or less, more preferably 5 to 60° C., and still more preferably 10 to 40° C. The temperature at the mixing is 80° C. or less, and thereby the stability of the silica raw material is comparatively high, and the gelation of the mixed liquid tends to be suppressed. The mixing time of the Nb aqueous solution and the silica raw material is preferably 1 minute to 6 hours, more preferably 10 minutes to 1 hour, and still more preferably 15 minutes to 40 minutes. The mixing time is 1 minute or more, and thereby the activity and the yield of acrylonitrile tend to be further improved. Further, the mixing time is 6 hours or less, and thereby the activity tends to be further improved.

From the viewpoints of suppressing nonuniform deposition of a Nb species and promoting the adsorption of the Nb species on a silica carrier, the molar ratio (Nb/Si) of Nb to 1 mol of Si in an aqueous mixed liquid B is preferably 0.02 to 0.7, more preferably 0.05 to 0.6, and still more preferably 0.06 to 0.5. The molar ratio of Nb is 0.02 or more, and thereby more of the Nb species tends to be able to be adsorbed and dispersed on the silica carrier. Further the molar ratio of Nb is 0.7 or less, and thereby the Nb species tends not to be nonuniformly deposited in a solution, and tends to be able to be efficiently adsorbed and dispersed on the silica carrier.

[Step (d)]

The step (d) is a step of mixing the aqueous mixed liquid A and the aqueous mixed liquid B to obtain an aqueous mixed liquid C. The mixing of the aqueous mixed liquid A and the aqueous mixed liquid B may be performed at any temperature as long as the temperature is a temperature at which the obtained aqueous mixed liquid C does not freeze or more, and does not boil or less. From the viewpoints of properly adjusting the oxidation/reduction state of the catalyst-constituting element, and of making the catalyst performance of the catalyst proper, and the like, the mixing temperature of the aqueous mixed liquid A and the aqueous mixed liquid B is preferably 20° C. or more and 80° C. or less.

[Step (d')]

The method for producing an oxide catalyst according to the present embodiment may comprises, after the step (d) and before the step (e), a step (d') of mixing the aqueous mixed liquid C, and powder silica and/or silica sol. From the viewpoint of making the catalyst performance of the obtained catalyst proper, the aqueous mixed liquid C and the powder silica are preferably mixed. The powder silica can be added as it is. More preferably, the powder silica is preferably added as a liquid in which powder silica is dispersed in water, i.e., a powder silica-containing suspension liquid. The concentration of the powder silica in the powder silica-containing suspension liquid at this time is preferably 1 to 30% by mass, more preferably 3 to 20% by mass, and still more preferably 4 to 18% by mass. The concentration of the powder silica is 1% by mass or more, and thereby the distorted shape of the catalyst particle caused by the low viscosity of the slurry tends to be able to be suppressed. The occurrence or the like of a depression in the catalyst particle also tends to be able to be suppressed. On the other hand, the concentration of the powder silica is 30% by mass or less, and thereby the gelling of a raw material blending liquid and clogging a pipeline caused by the high viscosity of a raw material blending liquid tend to be able to be avoided, making it possible to easily obtain a dried powder. Further, the catalyst performance also tends to be further improved.

The obtained aqueous mixed liquid may be subjected to an aging treatment. The aging means that the aqueous mixed liquid is left standstill or stirred for a predetermined time. An aging time is preferably 90 minutes or more and 50 hours or less, and more preferably 90 minutes or more and 6 hours or less. The aging time is within the above-mentioned range, and thereby the oxidation/reduction state (electric potential) of the aqueous mixed liquid easily becomes suitable and the catalyst performance of the obtained oxide catalyst tends to be further improved.

[Step (e)]

The step (e) is a step of drying the aqueous mixed liquid C to obtain a dried powder D. The drying can be performed by a known method, and can also be performed, for example, by spray drying or evaporation to dryness. When a fluidized-bed reaction method is adopted in the vapor-phase catalytic oxidation reaction or the vapor-phase catalytic ammoxidation reaction, a dried powder D in a minute sphere state is preferably obtained from the viewpoint of setting flowability within a reactor to a preferable state or the like. Therefore, the spray drying is preferably adopted. The atomization in the spray drying method may be carried out by a centrifugation method, a two-fluid nozzle method, or a high-pressure nozzle method. Air heated by steam or an electric heater or the like may be used as the heat source for drying.

A spray velocity, a velocity of the raw material blending liquid to be fed, and a rotation number of an atomizer in the case of the centrifugation method, or the like are preferably adjusted such that the size of the obtained dried powder is suitable. The mean particle diameter of the dried powder is preferably 35 to 75 μm, more preferably 40 to 70 μm, and still more preferably 45 to 65 μm. The mean particle diameter does not vary greatly even after calcining. The average particle diameter of the dried powder D can be measured by a method described in Examples.

[Step (f)]

The step (f) is a step of calcining a dried powder D to obtain an oxide catalyst. For example, a rotary furnace (rotary kiln) can be used as a calcining apparatus for calcining the dried powder D. The shape of a calcining machine for calcining the dried powder D therein is not particularly limited. The shape is preferably a tube shape (calcining tube) from the viewpoint of the fact that continuous calcining can be carried out, and particularly preferably a cylindrical shape. From the viewpoint of being likely to adjust a calcining temperature to a preferable rising temperature pattern or the like, a heating method is preferably an outer heating method. An electric furnace can be suitably used. The size and quality or the like of the calcining tube can be appropriately selected according to a calcining condition or a production amount.

The step of the calcination is preferably performed in two steps. When the first calcination is defined as pre-stage calcination and the subsequent calcination is defined as main calcination, it is preferable that the pre-stage calcination is performed in the temperature range of 250 to 400° C., and the main calcination is performed in the temperature range of 450 to 700° C. The pre-stage calcination and the main calcination may be continuously carried out. The main calcination may be carried out after the pre-stage calcination is completed once. The pre-stage calcination and the main calcination may be respectively divided into several steps.

The calcination may be performed in an atmospheric environment or in a circulation of air. However, from the viewpoint of adjusting the calcining atmosphere to a preferable oxidation/reduction state, at least a part of the calcination is preferably carried out while an inert gas which is substantially free from oxygen such as nitrogen is circulated. When the calcination is performed by a batch method, the amount of the inert gas to be supplied is preferably 50 NL/hr or more per 1 kg of the dried powder D from the viewpoint of adjusting the calcining atmosphere to a preferable oxidation/reduction state, more preferably 50 to 5000 NL/hr, and still more preferably 50 to 3000 NL/hr. Here, the term "NL" means a volume of a gas measured under standard temperature and pressure conditions, i.e., at 0° C. under a pressure condition of 1 atmosphere.

The reduction rate of the preliminarily calcined body is preferably 7 to 15%, more preferably 8 to 12%, and still more preferably 9 to 12%. The reduction rate is preferably within the above range from the viewpoint of a yield, catalyst production and the like. Specific examples of a method for controlling the reduction rate to a desired range include a method for changing the pre-stage calcination temperature, a method for adding an oxidizing component such as oxygen into an atmosphere during calcining, or a method for adding a reducing component into an atmosphere during calcining. They may be combined.

[Step (g)]

The production method according to the present embodiment may further comprise a step (g) of removing projection bodies present on the particle surface of the calcined body. Many projection bodies are projecting oxide crystals and other impurities. Particularly, in the case of the calcined body comprising a plurality of metals, the oxide having a composition different from that of the crystal forming a large part of the calcined body may be formed in such a shape that the oxide oozes out from the main part of the calcined body. Such a projection body becomes a factor of decreasing flowability. Therefore, the projection body is preferably removed from the catalyst surface. When the projection body is removed on a gram scale, the following apparatus can be used. That is, a perpendicular tube can be used, wherein a perforated plate having one or more holes is provided in a bottom part, and a paper filter is provided in an upper part. The calcined bodies are put in the perpendicular tube, and air is circulated from a lower part. Therefore, an air current flows from each hole, to urge the contact of the calcined bodies, and thereby the projection bodies can be removed.

[Oxide Catalyst]

An oxide catalyst according to the present embodiment is one produced by the above method for producing an oxide catalyst. The content of the silica in the oxide catalyst obtained by the production method according to the present embodiment is, in terms of $SiO_2$, with respect to the total amount of the oxide catalyst, preferably 20 to 70% by mass, more preferably 40 to 65% by mass, and still more preferably 40 to 60% by mass. The content of the silica is 20% by mass or more, and thereby the strength of the catalyst tends to be further improved. Further the content of the silica is 70% by mass or less, and thereby the catalyst tends to have a higher activity.

The oxide catalyst obtained by the production method according to the present embodiment preferably contains metal components represented by the following formula (1). The oxide catalyst contains the metal composition represented by the following formula (1), in the case where an unsaturated nitrile is produced by using the oxide catalyst, and thereby the selectivity of the unsaturated nitrile tends to be further improved.

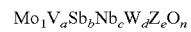

$$Mo_1V_aSb_bNb_cW_dZ_eO_n \qquad (1),$$

wherein the Z is at least one element selected from the group consisting of La, Ce, Pr, Yb, Y, Sc, Sr and Ba; a, b, c, d, e and n represent atomic ratios of the elements; and $0.1 \leq a < 0.3$, $0.15 \leq b \leq 0.5$, $0.01 \leq c \leq 0.5$, $0 \leq d \leq 0.4$, $0 \leq e \leq 0.2$, and n is a number determined by a, b, c, d and e.

[Method for Producing Unsaturated Nitrile]

A method for producing an unsaturated nitrile according to the present embodiment comprises a step of subjecting propane or isobutane to a vapor-phase catalytic oxidation reaction or a vapor-phase catalytic ammoxidation reaction by using an oxide catalyst produced by the above production method of the oxide catalyst, to produce a corresponding unsaturated nitrile. Hereinafter, a method for producing acrylonitrile by performing an ammoxidation reaction of propane by bringing propane, ammonia and an oxygen-containing gas into contact with the oxide catalyst according to the present embodiment filled in a reactor will be described.

(Feedstocks)

Propane and ammonia as feedstocks are not necessarily highly pure but those of industrial grade such as propane containing 3 vol % or less of impurities, for example, ethane, ethylene, n-butane, and isobutane, and ammonia containing about 3 vol % or less of impurities, for example, water can be used. There may be supplied to the reaction, as an oxygen-containing gas, for example, air, air enriched with oxygen, pure oxygen, or a gas diluted with inert gas such as helium, argon, carbon dioxide or nitrogen, or water vapor, but is not particularly limited thereto. When the gases are used on an industrial scale, among them, the air is preferably used from simplicity.

(Reaction Condition)

In the vapor-phase catalytic oxidation reaction of propane or isobutane, the reaction condition is not particularly limited, but the reaction may be performed under the following condition, for example. A molar ratio of oxygen to be supplied for the reaction to propane or isobutane is preferably 0.1 to 6, and more preferably 0.5 to 4. A reaction temperature is preferably 300 to 500° C., and more preferably 350 to 500° C. A reaction pressure is preferably $5 \times 10^4$ to $5 \times 10^5$ Pa, and more preferably $1 \times 10^5$ to $3 \times 10^5$ Pa. A contact time is preferably 0.1 to 10 (sec·g/cm³), and more preferably 0.5 to 5 (sec·g/cm³). By making the various conditions of the vapor-phase catalytic oxidation reaction in the above ranges, the generation of by-products tends to be further suppressed and the yield of an unsaturated nitrile tends to be further improved.

In the present embodiment, the contact time is defined by the following formula.

$$\text{Contact Time (sec·g/cm}^3) = (W/F) \times 273/(273+T)$$

Wherein, W, F, and T are defined as follows:
W=filled amount (g) of a catalyst;
F=flow rate (N cm³/sec) of a feedstock mixed gas under standard conditions (0° C., $1.013 \times 10^5$ Pa); and
T=reaction temperature (° C.).

In the vapor-phase catalytic ammoxidation reaction of propane or isobutane, the reaction condition is not particularly limited, but the reaction may be performed under the following condition, for example. A molar ratio of oxygen to be supplied for the reaction to propane or isobutane is preferably 0.1 to 6, and more preferably 0.5 to 4. A molar ratio of ammonia to be supplied for the reaction to propane or isobutane is preferably 0.3 to 1.5, and more preferably 0.7 to 1.2. A reaction temperature is preferably 350 to 500° C., and more preferably 380 to 470° C. A reaction pressure is preferably $5 \times 10^4$ to $5 \times 10^5$ Pa, and more preferably $1 \times 10^5$ to $3 \times 10^5$ Pa. A contact time is preferably 0.1 to 10 sec·g/cm$^3$, and more preferably 0.5 to 5 sec·g/cm$^3$. By making the various conditions of the vapor-phase catalytic ammoxidation reaction in the above ranges, the generation of by-products tends to be able to be further suppressed, and the yield of the unsaturated nitrile tends to be able to be further improved.

Conventional methods such as a fixed bed method, a fluidized bed method, and a moving bed method can be adopted as a reaction method in the vapor-phase catalytic oxidation reaction and the vapor-phase catalytic ammoxidation reaction. Among them, due to easiness of removal of a reaction heat, a fluidized bed reactor is preferable. The vapor-phase catalytic ammoxidation reaction may either be a single current system or a recycle system.

EXAMPLES

Hereinafter, the present embodiment will be described in more detail with reference to Examples and Comparative Examples, but the present embodiment is not limited to these Examples.

(Preparation of Niobium Mixed Liquid)

A niobium mixed liquid was prepared by the following method.

1.420 kg of niobic acid containing 79.8% by mass of $Nb_2O_5$ and 5.134 kg of oxalic acid dihydrate [$H_2C_2O_4.2H_2O$] were mixed in 10 kg of water. The molar ratio of oxalic acid/niobium charged was 4.8, and the concentration of niobium charged was 0.52 mol/kg. This liquid was heated and stirred at 95° C. for 2 hours to obtain a mixed liquid in which niobium was dissolved. The mixed liquid was allowed to stand still, and cooled with ice, and thereafter, the solid was filtered away by suction filtration to obtain a homogeneous niobium mixed liquid. The molar ratio of oxalic acid/niobium of the niobium mixed liquid was 2.340 by the following analysis.

(Analysis Method)

10 g of the niobium mixed liquid was precisely weighed in a crucible, dried at 95° C. overnight, and thereafter heat treated at 600° C. for 1 hour to obtain 0.8125 g of $Nb_2O_5$. From the result, the niobium concentration was 0.611 mol-Nb/kg-liquid. 3 g of the niobium mixed liquid was precisely weighed in a 300-mL glass beaker; 200 mL of hot water of about 80° C. was added; and then, 10 mL of a 1:1 sulfuric acid was added. The obtained mixed liquid was titrated using a ¼N $KMnO_4$ under stirring with the liquid being held at a liquid temperature of 70° C. on a hot stirrer. The point where a faint pale pink by $KMnO_4$ continued for about 30 sec or longer was taken as an end point. The concentration of oxalic acid was calculated from the titration amount by the following formula, and was 1.430 mol-oxalic acid/kg.

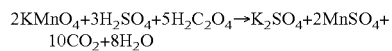

The obtained niobium mixed liquid was used as a niobium raw material liquid ($B_0$) in production of oxide catalysts of the following Examples 1 to 6 and Comparative Examples 1 and 2.

[Yield of Acrylonitrile (Unsaturated Nitrile)]

In Examples and Comparative Examples, the yield of acrylonitrile is based on the following definition. The molar number of the generated acrylonitrile was measured by previously analyzing a gas of acrylonitrile having a known concentration with gas chromatography (GC: manufactured by Shimadzu Corporation, product name: GC2014) to make a calibration curve, and thereafter injecting a certain amount of gas generated in an ammoxidation reaction into the GC.

Yield of Acrylonitrile (%)=(Molar Number of Generated Acrylonitrile)/(Molar Number of Supplied Propane)×100

The activity of a catalyst is based on the following definition. The molar number of unreacted propane was measured by injecting a certain amount of gas after the ammoxidation reaction to GC.

Activity of a catalyst=−ln(a molar number of unreacted propane (%)/100)×3.6(10$^3$ sec/h)/a contact time (sec·g/cm$^3$)×a bulk specific gravity of the catalyst (g/cm$^3$)

Example 1

(Preparation of Dried Powder)

A dried powder ($D_1$) was produced as follows.

To 1.520 g of water, 421.5 g of ammonium heptamolybdate [$(NH_4)_6Mo_7O_{24}.4H_2O$], 58.1 g of ammonium metavanadate [$NH_4VO_3$], 82.6 g of diantimony trioxide [$Sb_2O_3$], and 4.3 g of cerium nitrate [$Ce(NO_3)_3.6H_2O$] were added and heated at 95° C. for 1 hour with stirring, to prepare an aqueous mixed liquid ($A_1$).

After the obtained aqueous mixed liquid ($A_1$) was cooled to 70° C., 97.2 g of hydrogen peroxide water containing 30% by mass of $H_2O_2$ was added thereto, and continuously stirred at 55° C. for 30 minutes to prepare an aqueous mixed liquid ($A_2$).

To 460.5 g of a niobium mixed liquid ($B_0$) in which a molar ratio of oxalic acid/niobium was 2.340, 64.2 g of hydrogen peroxide water containing 30% by mass of $H_2O_2$ was added, and mixed at room temperature for 10 minutes with stirring to prepare an aqueous mixed liquid ($B_1$).

To the obtained aqueous mixed liquid ($B_1$), 710.6 g of silica sol containing 34.1% by mass of $SiO_2$ was added, and mixed at room temperature for 20 minutes to prepare an aqueous mixed liquid ($B_2$).

The aqueous mixed liquid ($B_2$), 30 g of an ammonium metatungstate aqueous solution (purity: 50%), and a dispersion liquid obtained by dispersing 210.5 g of powder silica in 3021.5 g of water were sequentially added to the aqueous mixed liquid ($A_2$), and the resultant mixture was then stirred and aged at 50° C. for 2.5 hours to obtain a slurry aqueous mixed liquid ($C_1$) as a raw material blending liquid. The obtained aqueous mixed liquid ($C_1$) was supplied to a centrifugal spray dryer (a drying heat source was air; and the same will apply hereafter) and dried to obtain a dried powder ($D_1$) in a minute sphere state. Temperatures at an inlet and an outlet of the dryer were respectively 210° C. and 120° C.

(Classification Operation)

The obtained dried powder ($D_1$) was classified using a sieve having an opening of 25 μm to obtain a dried powder ($D_2$) as a classified material. In the obtained dried powder ($D_2$), the content rate of particles of 25 μm or less was 0.2% by mass, and the mean particle diameter was 54 μm. The content rate of particles and the mean particle diameter were measured by LS230 (trade name) manufactured by BECKMAN COULTER (the same will apply hereafter).

(Calcination of Dried Powder ($D_2$))

The obtained dried powder ($D_2$) was supplied in the supplied amount of 80 g/hr to a continuous SUS cylindrical calcining tube which has a rotary furnace diameter (inner diameter; the same will apply hereafter) of 3 inches and a length of 89 cm. A nitrogen gas of 1.5 NL/min was flowed in a direction opposed to the supply direction of the dried powder (that is, countercurrent flow; the same will apply hereafter) and the same direction (that is, concurrent flow; the same will apply hereafter) respectively in the calcining tube, and the total flow rate was set to 3.0 NL/min. The temperature of the furnace was set such that the temperature of the calcining tube was raised over 4 hours to 360° C. as the maximum calcining temperature while the calcining tube was rotated at a speed of 4 rotation/min, and the temperature could be held at 360° C. for 1 hour, to perform pre-stage calcination. A small amount of the preliminary calcined body collected at the outlet of the calcining tube was sampled, and heated to 400° C. in a nitrogen atmosphere. The reduction rate was then measured. The reduction rate was 10.2%. The collected preliminary calcined body was supplied in the supplied amount of 60 g/hr to a continuous SUS cylindrical calcining tube which has a rotary furnace diameter of 3 inches and a length of 89 cm. A nitrogen gas of 1.1 NL/min was flowed in a direction opposed to the supply direction of the dried powder and the same direction respectively in the calcining tube, and the total flow rate was set to 2.2 NL/min. The temperature of the furnace was set such that the temperature could be raised to 680° C. over 2 hours, held at 680° C. for 2 hours, and then lowered to 600° C. over 8 hours, to obtain a calcined body ($D_3$) by performing main calcination.

(Removal of Projection Body)

50 g of a calcined body ($D_3$) was put in a perpendicular tube (inner diameter: 41.6 mm, length: 70 cm) wherein a perforated disk having three holes each having a diameter of 1/64 inches was provided in a bottom part and a paper filter was provided in an upper part. Then, air was circulated at room temperature towards the upper part from the lower part of the perpendicular tube via each hole, to urge the contact of the calcined bodies. An air current length in the direction in which the air current at this time flowed was 56 mm, and the mean linear speed of the air current was 332 m/s. The projection body was not present in the oxide catalyst ($E_1$) obtained after 24 hours.

The composition of the oxide catalyst ($E_1$) obtained as described above was measured by X-ray fluorescence analysis (apparatus: manufactured by Rigaku Corporation, RINT1000 (trade name), Cr tube, tube voltage: 50 kV, tube current: 50 mA, and the same will apply hereinafter). The obtained results are shown in Table 1.

(Ammoxidation Reaction of Propane)

Propane was provided for a vapor-phase catalytic ammoxidation reaction by the following method using the oxide catalyst ($E_1$) obtained above. A Vycor glass fluidized-bed reaction tube having an inner diameter of 25 mm was filled with 35 g of the composite oxide catalyst. A mixed gas having a molar ratio of propane:ammonia:oxygen:helium of 1:1:3:18 was supplied into the reaction tube at a contact time of 3.0 (sec·g/cm$^3$) at a reaction temperature of 440° C. under an atmospheric pressure as a reaction pressure. The reaction yields of acrylonitrile (AN) when a successive reaction was performed for 10 days for the catalyst are shown in Table 1.

Example 2

(Preparation of Dried Powder)

A dried powder ($D_1$) was produced as follows.

An aqueous mixed liquid ($A_1$) was prepared as in Example 1. After the obtained aqueous mixed liquid ($A_1$) was cooled to 70° C., 661.1 g of silica sol containing 34.1% by mass of $SiO_2$ was added thereto, and 97.2 g of hydrogen peroxide water containing 30% by mass of $H_2O_2$ was further added thereto, and continuously stirred at 55° C. for 30 minutes to prepare an aqueous mixed liquid ($A_2$).

To 460.5 g of a niobium mixed liquid ($B_0$) in which a molar ratio of oxalic acid/niobium was 2.340, 64.2 g of hydrogen peroxide water containing 30% by mass of $H_2O_2$ was added, and mixed at room temperature for 10 minutes with stirring to prepare an aqueous mixed liquid ($B_1$).

To the obtained aqueous mixed liquid ($B_1$), 49.5 g of silica sol containing 34.1% by mass of $SiO_2$ was added, and mixed at room temperature for 20 minutes to prepare an aqueous mixed liquid ($B_2$).

The aqueous mixed liquid ($B_2$), 30 g of an ammonium metatungstate aqueous solution (purity: 50%), and a dispersion liquid obtained by dispersing 210.5 g of powder silica in 3021.5 g of water were sequentially added to the aqueous mixed liquid ($A_2$), and the resultant mixture was then stirred and aged at 50° C. for 2.5 hours to obtain a slurry aqueous mixed liquid ($C_1$) as a raw material blending liquid. The obtained aqueous mixed liquid ($C_1$) was supplied to a centrifugal spray dryer (a drying heat source was air; and the same will apply hereafter) and dried to obtain a dried powder ($D_1$) in a minute sphere state. Temperatures at an inlet and an outlet of the dryer were respectively 210° C. and 120° C.

A catalyst was prepared under the same condition of the classification operation and the like thereafter as in Example 1, to obtain an oxide catalyst ($E_1$). Then, the ammoxidation reaction of propane was performed by the same method as that in Example 1 using the catalysts.

Example 3

(Preparation of Dried Powder)

A dried powder ($D_1$) was produced as follows.

An aqueous mixed liquid ($A_1$) was prepared as in Example 1. After the obtained aqueous mixed liquid ($A_1$) was cooled to 70° C., 29.9 g of silica sol containing 34.1% by mass of $SiO_2$ was added thereto, and 97.2 g of hydrogen peroxide water containing 30% by mass of $H_2O_2$ was further added thereto, and continuously stirred at 55° C. for 30 minutes to prepare an aqueous mixed liquid ($A_2$).

To 460.5 g of a niobium mixed liquid ($B_0$) in which a molar ratio of oxalic acid/niobium was 2.340, 64.2 g of hydrogen peroxide water containing 30% by mass of $H_2O_2$ was added, and mixed at room temperature for 10 minutes with stirring to prepare an aqueous mixed liquid ($B_1$).

To the obtained aqueous mixed liquid ($B_1$), 1267.8 g of silica sol containing 34.1% by mass of $SiO_2$ was added, and mixed at room temperature for 20 minutes to prepare an aqueous mixed liquid ($B_2$).

The aqueous mixed liquid ($B_2$), 30 g of an ammonium metatungstate aqueous solution (purity: 50%), and a dispersion liquid obtained by dispersing 20.5 g of powder silica in 294.8 g of water were sequentially added to the aqueous mixed liquid ($A_2$), and the resultant mixture was then stirred and aged at 50° C. for 2.5 hours to obtain a slurry aqueous mixed liquid ($C_1$) as a raw material blending liquid. The obtained aqueous mixed liquid ($C_1$) was supplied to a centrifugal spray dryer (a drying heat source was air; and the same will apply hereafter) and dried to obtain a dried powder ($D_1$) in a minute sphere state. Temperatures at an inlet and an outlet of the dryer were respectively 210° C. and 120° C.

A catalyst was prepared under the same condition of the classification operation and the like thereafter as in Example 1, to obtain an oxide catalyst ($E_1$). Then, the ammoxidation reaction of propane was performed by the same method as that in Example 1 using the catalysts.

Example 4

A catalyst was prepared under the same condition as in Example 1, except for altering the mixing time of the aqueous mixed liquid ($B_1$) and the silica sol to 30 sec, to obtain an oxide catalyst ($E_1$). Then, the ammoxidation reaction of propane was performed by the same method as that in Example 1 using the catalysts.

Example 5

(Preparation of Dried Powder)

An aqueous mixed liquid ($A_1$) was prepared as in Example 1. After the obtained aqueous mixed liquid ($A_1$) was cooled to 70° C., 628.1 g of silica sol containing 34.1% by mass of $SiO_2$ was added thereto, and 97.2 g of hydrogen peroxide water containing 30% by mass of $H_2O_2$ was further added thereto, and continuously stirred at 55° C. for 30 minutes to prepare an aqueous mixed liquid ($A_2$).

To 460.5 g of a niobium mixed liquid ($B_0$) in which a molar ratio of oxalic acid/niobium was 2.340, 64.2 g of hydrogen peroxide water containing 30% by mass of $H_2O_2$ was added, and mixed at room temperature for 10 minutes with stirring to prepare an aqueous mixed liquid ($B_1$).

To the obtained aqueous mixed liquid ($B_1$), 82.5 g of silica sol containing 34.1% by mass of $SiO_2$ was added, and mixed at room temperature for 20 minutes to prepare an aqueous mixed liquid ($B_2$).

The aqueous mixed liquid ($B_2$), 30 g of an ammonium metatungstate aqueous solution (purity: 50%), and a dispersion liquid obtained by dispersing 210.5 g of powder silica in 3021.5 g of water were sequentially added to the aqueous mixed liquid ($A_2$), and the resultant mixture was then stirred and aged at 50° C. for 2.5 hours to obtain a slurry aqueous mixed liquid ($C_1$) as a raw material blending liquid. The obtained aqueous mixed liquid ($C_1$) was supplied to a centrifugal spray dryer (a drying heat source was air; and the same will apply hereafter) and dried to obtain a dried powder ($D_1$) in a minute sphere state. Temperatures at an inlet and an outlet of the dryer were respectively 210° C. and 120° C.

A catalyst was prepared under the same condition of the classification operation and the like thereafter as in Example 1, to obtain an oxide catalyst ($E_1$). Then, the ammoxidation reaction of propane was performed by the same method as that in Example 1 using the catalysts.

Example 6

A catalyst was prepared under the same condition as in Example 2, except for altering the mixing time of the aqueous mixed liquid ($B_1$) and the silica sol to 30 sec, to obtain an oxide catalyst ($E_1$). Then, the ammoxidation reaction of propane was performed by the same method as that in Example 1 using the catalysts.

Comparative Example 1

(Preparation of Dried Powder)

A dried powder (D') was produced as follows. An aqueous mixed liquid ($A_1$) was prepared as in Example 1. After the obtained aqueous mixed liquid ($A_1$) was cooled at 70° C., 710.6 g of silica sol containing 34.1% by mass of $SiO_2$ was added thereto, and 97.2 g of hydrogen peroxide water containing 30% by mass of $H_2O_2$ was further added thereto, and continuously stirred at 55° C. for 30 minutes to prepare an aqueous mixed liquid (A').

To 460.5 g of the niobium mixed liquid ($B_0$) in which a molar ratio of oxalic acid/niobium of 2.340, 64.2 g of hydrogen peroxide water containing 30% by mass of $H_2O_2$ was added, and mixed at room temperature for 10 minutes with stirring to prepare an aqueous mixed liquid ($B_1$).

The aqueous mixed liquid ($B_1$), 30 g of an ammonium metatungstate aqueous solution (purity: 50%), and a dispersion liquid obtained by dispersing 210.5 g of powder silica in 2841.8 g of water were sequentially added to the aqueous mixed liquid (A'), and the resultant mixture was then stirred and aged at 50° C. for 2.5 hours to obtain a slurry aqueous mixed liquid (C') as a raw material blending liquid. The obtained aqueous mixed liquid (C') was supplied to a centrifugal spray dryer (a drying heat source was air; and the same will apply hereafter) and dried to obtain a dried powder (D') in a minute sphere state. Temperatures at an inlet and an outlet of the dryer were respectively 210° C. and 120° C.

The powder was classified and calcined by the same method as in Example 1, and the ammoxidation reaction of propane was performed by the same method as that in Example 1 using the catalysts.

Comparative Example 2

A dried powder ($D_1$) was prepared by the same method as in Example 1, except for adding 10.6 g of silica sol to the aqueous mixed liquid ($A_2$) in place of adding 710.6 g of silica sol to the aqueous mixed liquid ($A_1$), and sequentially adding the silica sol, the aqueous mixed liquid ($B_1$), the ammonium metatungstate aqueous solution, and the dispersion liquid in which the powder silica was dispersed to the aqueous mixed liquid ($A_2$). Then, the powder was classified and calcined, and the ammoxidation reaction of propane was performed by the same method as that in Example 1 using the catalysts.

Example 7

(Preparation of Dried Powder)

A dried powder ($D_1$) was produced as follows.

To 1,557 g of water, 432.1 g of ammonium heptamolybdate [$(NH_4)_6Mo_7O_{24}.4H_2O$], 59.9 g of ammonium metavanadate [$NH_4VO_3$], 84.3 g of diantimony trioxide [$Sb_2O_3$], and 4.8 g of cerium nitrate [$Ce(NO_3)_2.6H_2O$] were added and heated at 95° C. for 1 hour with stirring, to prepare an aqueous mixed liquid ($A_1$).

After the obtained aqueous mixed liquid ($A_1$) was cooled to 70° C., 98.4 g of hydrogen peroxide water containing 30% by mass of $H_2O_2$ was added thereto, and continuously stirred at 55° C. for 30 minutes to prepare an aqueous mixed liquid ($A_2$).

To 378.4 g of the niobium mixed liquid ($B_0$) in which a molar ratio of oxalic acid/niobium of 2.340, 66.3 g of hydrogen peroxide water containing 30% by mass of $H_2O_2$ was added, and mixed at room temperature for 10 minutes with stirring to prepare an aqueous mixed liquid ($B_1$).

To the obtained aqueous mixed liquid ($B_1$), 807.8 g of silica sol containing 34.1% by mass of $SiO_2$ was added, and mixed at room temperature for 20 minutes with stirring to prepare an aqueous mixed liquid ($B_2$).

The aqueous mixed liquid ($B_2$), 31.0 g of an ammonium metatungstate aqueous solution (purity: 50%), and a dispersion liquid obtained by dispersing 211.5 g of powder silica in 2850 g of water were sequentially added to the aqueous mixed liquid ($A_2$), and the resultant mixture was then stirred and aged at 50° C. for 2.5 hours to obtain a slurry aqueous mixed liquid ($C_1$) as a raw material blending liquid. The obtained aqueous mixed liquid ($C_1$) was supplied to a centrifugal spray dryer (a drying heat source was air; and the same will apply hereafter) and dried to obtain a dried powder ($D_1$) in a minute sphere state. Temperatures at an inlet and an outlet of the dryer were respectively 210° C. and 120° C.

(Classification Operation)

The obtained dried powder ($D_1$) was classified using a sieve having an opening of 25 μm to obtain a dried powder ($D_2$) as a classified material. In the obtained dried powder ($D_2$), the content rate of particles of 25 μm or less was 0.2% by mass, and the mean particle diameter was 54 μm. The content rate of particles and the mean particle diameter were measured by LS230 (trade name) manufactured by BECKMAN COULTER (the same will apply hereafter).

(Calcination of Dried Powder ($D_2$))

The obtained dried powder ($D_2$) was supplied in the supplied amount of 80 g/hr to a continuous SUS cylindrical calcining tube which has a rotary furnace diameter (inner diameter; the same will apply hereafter) of 3 inches and a length of 89 cm. A nitrogen gas of 1.5 NL/min was flowed in a direction opposed to the supply direction of the dried powder (that is, countercurrent flow; the same will apply hereafter) and the same direction (that is, concurrent flow; the same will apply hereafter) respectively in the calcining tube, and the total flow rate was set to 3.0 NL/min. The temperature of the furnace was set such that the temperature of the calcining tube was raised over 4 hours to 360° C. as the maximum calcining temperature while the calcining tube was rotated at a speed of 4 rotation/min, and the temperature could be held at 360° C. for 1 hour, to perform pre-stage calcination. A small amount of the preliminarily calcined body collected at the outlet of the calcining tube was sampled, and heated to 400° C. in a nitrogen atmosphere. The reduction rate was then measured. The reduction rate was 10.2%. The collected preliminarily calcined body was supplied in the supplied amount of 60 g/hr to a continuous SUS cylindrical calcining tube which has a rotary furnace diameter 3 inches and a length of 89 cm. A nitrogen gas of 1.1 NL/min was flowed in a direction opposed to the supply direction of the dried powder and the same direction respectively in the calcining tube, and the total flow rate was set at 2.2 NL/min. The temperature of the furnace was set such that the temperature could be raised to 680° C. over 2 hours, held at 680° C. for 2 hours, and then lowered to 600° C. over 8 hours, to perform main calcination to obtain a calcined body ($D_3$).

(Removal of Projection Body)

50 g of a calcined body ($D_3$) was put in a perpendicular tube (inner diameter: 41.6 mm, length: 70 cm) wherein a perforated disk having three holes each having a diameter of 1/64 inches was provided in a bottom part and a paper filter was provided in an upper part. Then, air was circulated at room temperature towards the upper part from the lower part of the perpendicular tube via each hole, to urge the contact of the calcined bodies. An air current length in the direction in which the air current at this time flowed was 56 mm, and the mean linear speed of the air current was 332 m/s. The projection body was not present in the oxide catalyst ($E_1$) obtained after 24 hours.

(Ammoxidation Reaction of Propane)

Propane was supplied for a vapor-phase catalytic ammoxidation reaction by the following method using the oxide catalyst ($E_1$) obtained above. A Vycor glass fluidized-bed reaction tube having an inner diameter of 25 mm was filled with 35 g of the oxide catalyst. A mixed gas having a molar ratio of propane:ammonia:oxygen:helium of 1:1:3:18 was supplied into the reaction tube at a contact time of 3.0 (sec·g/cm$^3$) at a reaction temperature of 440° C. under an atmospheric pressure as a reaction pressure. The reaction yields of acrylonitrile (AN) when a successive reaction was performed for 10 days for the catalyst are shown in Table 1.

Example 8

(Preparation of Dried Powder)

A dried powder ($D_1$) was produced as follows.

An aqueous mixed liquid ($A_1$) was prepared as in Example 7. After the obtained aqueous mixed liquid ($A_1$) was cooled to 70° C., 760.3 g of silica sol containing 34.0% by mass of $SiO_2$ was added thereto, and 98.4 g of hydrogen peroxide water containing 30% by mass of $H_2O_2$ was further added thereto, and continuously stirred at 55° C. for 30 minutes to prepare an aqueous mixed liquid ($A_2$).

To 378.4 g of a niobium mixed liquid ($B_0$) in which a molar ratio of oxalic acid/niobium was 2.340, 66.3 g of hydrogen peroxide water containing 30% by mass of $H_2O_2$ was added, and mixed at room temperature for 10 minutes with stirring to prepare an aqueous mixed liquid ($B_1$).

To the obtained aqueous mixed liquid ($B_1$), 47.5 g of silica sol containing 34.0% by mass of $SiO_2$ was added, and mixed at room temperature for 20 minutes to prepare an aqueous mixed liquid ($B_2$).

The aqueous mixed liquid ($B_2$), 31.0 g of an ammonium metatungstate aqueous solution (purity: 50%), and a dispersion liquid obtained by dispersing 211.5 g of powder silica in 2850 g of water were sequentially added to the aqueous mixed liquid ($A_2$), and the resultant mixture was then stirred and aged at 50° C. for 2.5 hours to obtain a slurry aqueous mixed liquid ($C_1$) as a raw material blending liquid. The obtained aqueous mixed liquid ($C_1$) was supplied to a centrifugal spray dryer (a drying heat source was air; and the same will apply hereafter) and dried to obtain a dried powder ($D_1$) in a minute sphere state. Temperatures at an inlet and an outlet of the dryer were respectively 210° C. and 120° C.

A catalyst was prepared under the same condition of the classification operation and the like thereafter as in Example 7, to obtain an oxide catalyst ($E_1$). Then, the ammoxidation reaction of propane was performed by the same method as that in Example 7 using the catalysts.

Example 9

A catalyst was prepared under the same condition as in Example 7, except for altering the mixing time of the aqueous mixed liquid ($B_1$) and the silica sol to 30 sec, to obtain an oxide catalyst ($E_1$). Then, the ammoxidation reaction of propane was performed by the same method as that in Example 7 using the catalysts.

Example 10

A catalyst was prepared under the same condition as in Example 8, except for altering the mixing time of the aqueous mixed liquid (B₁) and the silica sol to 30 sec, to obtain an oxide catalyst (E₁). Then, the ammoxidation reaction of propane was performed by the same method as that in Example 8 using the catalysts.

Comparative Example 3

(Preparation of Dried Powder)

A dried powder (D') was produced as follows. An aqueous mixed liquid (A₁) was prepared as in Example 7. After the obtained aqueous mixed liquid (A₁) was cooled to 70° C., 807.8 g of silica sol containing 34.0% by mass of SiO₂ was added thereto, and 98.4 g of hydrogen peroxide water containing 30% by mass of H₂O₂ was further added thereto, and continuously stirred at 55° C. for 30 minutes to prepare an aqueous mixed liquid (A').

To 378.4 g of the niobium mixed liquid (B₀) in which a molar ratio of oxalic acid/niobium of 2.340, 66.3 g of hydrogen peroxide water containing 30% by mass of H₂O₂ was added, having and mixed at room temperature for 10 minutes with stirring to prepare an aqueous mixed liquid (B₁).

The aqueous mixed liquid (B₁), 31.0 g of an ammonium metatungstate aqueous solution (purity: 50%), and a dispersion liquid obtained by dispersing 242.5 g of powder silica in 3480.8 g of water were sequentially added to the aqueous mixed liquid (A'), and the resultant mixture was then stirred and aged at 50° C. for 2.5 hours to obtain a slurry aqueous mixed liquid (C') as a raw material blending liquid. The obtained aqueous mixed liquid (C') was supplied to a centrifugal spray dryer (a drying heat source was air; and the same will apply hereafter) and dried to obtain a dried powder (D') in a minute sphere state. Temperatures at an inlet and an outlet of the dryer were respectively 210° C. and 120° C.

The powder was classified and calcined by the same methods as in Example 7, and the ammoxidation reaction of propane was performed using the catalyst.

There are shown in Table 1 the activities and the yields of the reactions using the catalysts indicated in Examples 1 to 10 and Comparative Examples 1 to 3.

TABLE 1

| | Nb/Si * | Activity | Acrylonitrile Yield (%) | Catalyst Composition |
|---|---|---|---|---|
| Example 1 | 0.070 | 2.65 | 54.2 | $Mo_1V_{0.206}Sb_{0.220}Nb_{0.131}W_{0.030}Ce_{0.005}$ |
| Example 2 | 1.000 | 2.58 | 54.0 | |
| Example 3 | 0.040 | 2.54 | 53.6 | |
| Example 4 | 0.070 | 2.55 | 53.7 | |
| Example 5 | 0.600 | 2.57 | 53.4 | |
| Example 6 | 1.000 | 2.55 | 53.3 | |
| Comparative Example 1 | 0.070 | 2.50 | 52.8 | |
| Comparative Example 2 | 0.070 | 2.50 | 52.9 | |

TABLE 1-continued

| | Nb/Si * | Activity | Acrylonitrile Yield (%) | Catalyst Composition |
|---|---|---|---|---|
| Example 7 | 0.050 | 2.70 | 56.1 | $Mo_1V_{0.207}Sb_{0.218}Nb_{0.102}W_{0.030}Ce_{0.005}$ |
| Example 8 | 0.850 | 2.63 | 55.9 | |
| Example 9 | 0.050 | 2.55 | 55.8 | |
| Example 10 | 0.850 | 2.56 | 55.7 | |
| Comparative Example 3 | 0.050 | 2.53 | 55.5 | |

*: a molar ratio (Nb/Si) of Nb to 1 mol of Si in an aqueous mixed liquid B

According to the following condition in the case where the yield was raised by 0.5% and CO$_X$ as by-products was instead decreased by 0.5%, nearly 80,000 tons of CO$_X$ is enabled to be decreased in one year. From the viewpoint of being able to cut down CO$_X$ as greenhouse gases in such a large scale, Examples 1 to 10 attain a more advantageous effect than Comparative Examples 1 to 3.

(Condition)

World production capacity of acrylonitrile: about 6,000,000 tons/year

Before the improvement, AN yield: 53%, CO$_X$: 19%

After the improvement, AN yield: 53.5%, CO$_X$: 18.5%

INDUSTRIAL APPLICABILITY

An oxide catalyst, being produced by the method of the present invention has an industrial applicability as a catalyst such as an unsaturated nitrile.

The invention claimed is:

1. A method for producing an oxide catalyst, the method comprising:
   a step (a) of obtaining an aqueous mixed liquid A comprising Mo, V and Sb;
   a step (b) of mixing a Nb raw material which is one or more selected from the group consisting of niobic acid, and inorganic niobate and an organic niobate, water and an organic acid to obtain a Nb aqueous solution;
   a step (c) of mixing the Nb aqueous solution and a silica raw material to obtain an aqueous mixed liquid B;
   a step (d) of mixing the aqueous mixed liquid A and the aqueous mixed liquid B to obtain an aqueous mixed liquid C;
   a step (e) of drying the aqueous mixed liquid C to obtain a dried powder D; and
   a step (f) of calcining the dried powder D to obtain the oxide catalyst,
   wherein the oxide catalyst consists of a metal component represented by formula (1):

$$Mo_1V_aSb_bNb_cW_dZ_eO_n \qquad (1),$$

wherein Z is at least one element selected from the group consisting of La, Ce, Pr, Yb, Y, Sc, Sr and Ba; a, b, c, d, e and n represent atomic ratios of each element and satisfy $0.1 \leq a \leq 0.3$, $0.15 \leq b \leq 0.5$, $0.01 \leq c \leq 0.5$, $0 \leq d \leq 0.4$, and $0 \leq e \leq 0.2$, and n is a number determined by a, b, c, d and e.

2. The method for producing the oxide catalyst according to claim 1, wherein a molar ratio (Nb/Si) of Nb to 1 mol of Si in the aqueous mixed liquid B is 0.02 to 0.7.

3. The method for producing the oxide catalyst according to claim 1, wherein in the step (c), a mixing time of the Nb aqueous solution and the silica raw material is 1 minute to 6 hours.

4. The method for producing the oxide catalyst according to claim 1, comprising, after the step (d) and before the step (e), a step (d') of mixing the aqueous mixed liquid C and powder silica and/or silica sol.

5. The method for producing the oxide catalyst according to claim 1, wherein a content of silica in the oxide catalyst is 20 to 70% by mass in terms of $SiO_2$.

\* \* \* \* \*